United States Patent
Boebel et al.

(10) Patent No.: US 9,862,686 B2
(45) Date of Patent: *Jan. 9, 2018

(54) N1-SULFONYL-5-FLUOROPYRIMIDINONE DERIVATIVES

(71) Applicant: Adama Makhteshim Ltd., Airport (IL)

(72) Inventors: Timothy Boebel, Indianapolis, IN (US); Kristy Bryan, Carmel, IN (US); Beth Lorsbach, Indianapolis, IN (US); W. John Owen, Indianapolis, IN (US); Jeffery D. Webster, New Palestine, IN (US); Chenglin Yao, Westfield, IN (US); Mark A. Pobanz, Zionsville, IN (US); Scott Thornburgh, Carmel, IN (US); Timothy P. Martin, Noblesville, IN (US)

(73) Assignee: ADAMA MAKHTESHIM LTD., Airport (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/661,274

(22) Filed: Mar. 18, 2015

(65) Prior Publication Data

US 2015/0191436 A1 Jul. 9, 2015

Related U.S. Application Data

(63) Continuation of application No. 12/851,357, filed on Aug. 5, 2010, now Pat. No. 9,006,259.

(60) Provisional application No. 61/232,204, filed on Aug. 7, 2009.

(51) Int. Cl.
| | |
|---|---|
| A01N 43/54 | (2006.01) |
| C07D 239/46 | (2006.01) |
| C07D 239/47 | (2006.01) |
| A01N 47/24 | (2006.01) |
| A01N 47/36 | (2006.01) |
| C07D 401/12 | (2006.01) |
| C07D 403/12 | (2006.01) |
| C07D 409/12 | (2006.01) |
| A01N 47/08 | (2006.01) |

(52) U.S. Cl.
CPC .......... *C07D 239/47* (2013.01); *A01N 43/54* (2013.01); *A01N 47/08* (2013.01); *A01N 47/24* (2013.01); *A01N 47/36* (2013.01); *C07D 239/46* (2013.01); *C07D 401/12* (2013.01); *C07D 403/12* (2013.01); *C07D 409/12* (2013.01)

(58) Field of Classification Search
CPC .............................. A01N 43/54; C07D 239/46
See application file for complete search history.

(56) References Cited

U.S. PATENT DOCUMENTS

| | | |
|---|---|---|
| 3,309,359 A | 3/1967 | Duschinsky et al. |
| 3,368,938 A | 2/1968 | Berger et al. |
| 3,868,373 A | 2/1975 | Hoffer |
| 4,845,081 A | 7/1989 | Sloan |
| 4,996,208 A | 2/1991 | Lidner et al. |
| 5,962,489 A | 10/1999 | Mueller et al. |
| 6,066,638 A | 5/2000 | Bereznak et al. |
| 6,617,330 B2 | 9/2003 | Walter |
| 7,914,799 B2 | 3/2011 | Jira et al. |
| 2003/0039667 A1 | 2/2003 | Jira et al. |
| 2008/0004253 A1 | 1/2008 | Branstetter et al. |
| 2008/0269238 A1 | 10/2008 | Sugihara et al. |
| 2009/0203647 A1 | 8/2009 | Benko et al. |
| 2010/0022538 A1 | 1/2010 | Boebel et al. |
| 2011/0034493 A1 | 2/2011 | Boebel et al. |

FOREIGN PATENT DOCUMENTS

| | | |
|---|---|---|
| EP | 0102908 A1 | 3/1984 |
| EP | 0139613 A1 | 5/1985 |
| EP | 0332579 A2 | 9/1989 |
| EP | 08/77022 A1 | 11/1998 |
| EP | 0877022 B1 | 4/2003 |
| GB | 1461184 A | 1/1977 |
| JP | 6001793 A | 1/1994 |
| WO | WO97/33890 A1 | 9/1997 |
| WO | WO02/30922 A2 | 4/2002 |
| WO | WO2008/083465 A1 | 7/2008 |
| WO | WO2009/094442 A2 | 7/2009 |
| WO | WO2010/047866A2 A2 | 4/2010 |
| WO | WO2010/085377A2 A2 | 7/2010 |

OTHER PUBLICATIONS

Utah Valley University. © 2009. Available from: < http://science.uvu.edu/ochem/index.php/alphabetical/a-b/alkenyl-group/ >.*
Ledochowski, Z., et al. Roczniki Chemii. (1967), vol. 41, pp. 215-220.
International Search Report and Written Opinion for PCT/US2012/050930, Oct. 15, 2012.
International Search Report for PCT/US2010/044579, Sep. 21, 2010.
Chiacchio U, et al., Enantioselective Syntheses and Cytotoxicity of N, O-Nucleosides, Journal of Medicinal Chemistry, Jan. 1, 2003, vol. 46, pp. 3696-3702.
Morris J. Robins, et al., A direct synthesis of 5-fluorocytosine and its nucleosides using trifluoromethyl hypofluorite, Journal of the Chemical Society, Chemical Communications, No. 1, Jan. 1, 1972, p. 18.
Arthur F. Lewis et al., Synthesis and in vitro anti-human cytomegalovirus (hcmv) activity of certain alkenyl substituted cytosines and 5-halocytosines, Journal of Heterocyclic Chemistry, Sep. 1, 1995, vol. 32, No. 5, pp. 1513-1515.
Kulikowski et al., Methylation and tautomerism of 5-fluorocytosine nucleosides and their analogues. Journal Nucleic Acids Research, Jan. 1, 2978, vol. 4, pp. S7-S10, © Jan. 1, 1978.

(Continued)

*Primary Examiner* — Noble Jarrell
*Assistant Examiner* — John S Kenyon
(74) *Attorney, Agent, or Firm* — Gary J. Gershik; Cooper & Dunham LLP

(57) ABSTRACT

This present disclosure is related to the field of N1-sulfonyl-5-fluoropyrimidinones and their derivatives and to the use of these compounds as fungicides.

13 Claims, No Drawings

(56) References Cited

OTHER PUBLICATIONS

Supplemental European Search Report for EP10807172 (PCT/US2010/044579), Dec. 7, 2012.
International Search Report for PCT/US2010/044592, Sep. 21, 2010.
International Search Report for PCT/US2009/031683, Jan. 22, 2009.
Jaworski et al., Infrared spectra and tautomerism of 5-fluorocytosine, 5-bromocytosine and 5-iodocytosine, Matrix isolation and theoretical ab initio studies, Journal of Molecular Structure, Jan. 1, 1990, vol. 223, pp. 63-92.
Gabriella et al., Some 5-fluorosulfanilamidopyrimidines, Gazzetta Chimica Italiana, Jan. 1, 1963, vol. 93, No. 10, pp. 1268-1278.
Zhang et al., Improved method for synthesis of 5-fluorocytosine (5-FC). CAPLUS Abstract 111:134074 (1989).
International Search Report for PCT/US2011/020351, Mar. 14, 2011.
Liang et al., A facile synthesis and herbicidal activities of novel fluorine-containing thiazolo[4, 5-d] pyrimidin-7(6H)-ones, Journal of Fluorine Chemistry [online], Jul. 2007, vol. 128, Issue 7, pp. 579-884.
Bera et al., Nucleosides with furanyl scaffolds, Tetrahedron, Jun. 10, 2002, vol. 58, No. 24, pp. 4865-4871.
Duschinsky et all, Cytosine derivatives, CAPLUS Abstract 61:18527, 1964.
International Search Report for PCT/US2010/044588, Oct. 1, 2010.
International Search Report for PCT/US2012/050931, Oct. 9, 2012.
International Search Report for PCT/US2010/060792, Apr. 22, 2011.
Waring, MJ, Defining optimum lipophilicity and molecular weight ranges for drug candidates—Molecular weight dependent lower logD limits based on permeability, Bioorganic & Medical Chemistry Letters, May 15, 2009, vol. 19, No. 10, pp. 2844-2851.
International Search Report for PCT/US2010/044576, Sep. 23, 2010.
Duschinsky et al., Nucleosides, XXXIII, N4-Acylated 5-Flurocytosines and a Direct Synthesis of 5-Fluoro-2'-deoxycytidine, Journal of Medicinal Chemistry, Jul. 1, 1996, vol. 9, No. 4, pp. 566-572.
European Patent Office, Supplementary European Search Report and European Search Opinion for EP 10 807 177.0-2101 PCT/US2010/044592, dated Nov. 15, 2012, 4 pages.
International Searching Authority, International Search Report, Written Opinion, and International Preliminary Report on Patentability for PCT/US2010/0445592, dated Feb. 7, 2012, 13 pages.

\* cited by examiner

N1-SULFONYL-5-FLUOROPYRIMIDINONE DERIVATIVES

CROSS REFERENCE TO RELATED APPLICATIONS

This application is a continuation application of U.S. patent application Ser. No. 12/851,357, filed Aug. 5, 2010, which claims the benefit of U.S. Provisional Patent Application Ser. No. 61/232,204, filed Aug. 7, 2009.

BACKGROUND AND SUMMARY OF THE INVENTION

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to N1-sulfonyl-5-fluoropyrimidinone compounds and their use as fungicides. The compounds of the present disclosure may offer protection against ascomycetes, basidiomycetes, deuteromycetes and oomycetes.

One embodiment of the present disclosure may include compounds of Formula I:

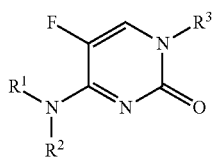

Formula I wherein $R^1$ is:
H;
$C_1$-$C_6$ alkyl optionally substituted with 1-3 $R^4$;
$C_1$-$C_6$ alkenyl optionally substituted with 1-3 $R^4$;
$C_3$-$C_6$ alkynyl optionally substituted with 1-3 $R^4$;
phenyl or benzyl wherein each of the phenyl or the benzyl may be optionally substituted with 1-3 $R^5$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^5$, biphenyl or naphthyl optionally substituted with 1-3 $R^5$;
—(CHR$^6$)$_m$OR$^7$;
—C(=O)R$^8$;
—C(=S)R$^8$;
—C(=O)OR$^8$;
—C(=S)OR$^8$;
—S(O)$_2$R$^8$;
—(CHR$^6$)$_m$N(R$^9$)R$^{10}$;
—C(=O)N(R$^9$)R$^{10}$; or
—C(=S)N(R$^9$)R$^{10}$;
wherein m is an integer 1-3;
$R^2$ is:
H; or
$C_1$-$C_6$ alkyl optionally substituted with $R^4$;
alternatively $R^1$ and $R^2$ may be taken together to form =CR$^{11}$N(R$^{12}$)R$^{13}$;
$R^3$ is —S(O)$_2$R$^{14}$;
$R^4$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, halothio, $C_1$-$C_3$ alkylamino, $C_2$-$C_6$ alkoxycarbonyl, $C_2$-$C_6$ alkylcarbonyl, $C_2$-$C_6$ alkylaminocarbonyl, hydroxyl, or $C_3$-$C_6$ trialkylsilyl;
$R^5$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, halothio, amino, $C_1$-$C_6$ alkylamino, dialkylamino, $C_2$-$C_6$ alkoxycarbonyl, $C_1$-$C_6$ alkylsulfonyl or $C_2$-$C_6$ alkylcarbonyl, nitro, hydroxyl, or cyano;
$R^6$ is H, $C_1$-$C_6$ alkyl, $C_1$-$C_6$ alkoxy, phenyl or benzyl wherein each of the benzyl or the phenyl may be optionally substituted with 1-3 $R^5$;
$R^7$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, $C_2$-$C_6$ alkylcarbonyl, phenyl or benzyl wherein each of the phenyl or the benzyl may be optionally substituted with 1-3 $R^5$, or with a 5- or 6-membered saturated or unsaturated ring system, or with 5-6 fused ring system, or with a 6-6 fused ring system each containing 1-3 heteroatoms wherein each ring may be optionally substituted with 1-3 $R^5$, biphenyl or naphthyl optionally substituted with 1-3 $R^5$;
$R^8$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, phenyl or benzyl wherein each of the phenyl or the benzyl may be optionally substituted with 1-3 $R^5$, or with a 5- or 6-membered saturated or unsaturated ring system, or with a 5-6 fused ring system, or 6-6 fused ring system each containing 1-3 heteroatoms wherein each ring may be optionally substituted with 1-3 $R^5$, biphenyl or naphthyl optionally substituted with 1-3 $R^5$;
$R^9$ is H, $C_1$-$C_6$ alkyl, $C_1$-$C_6$ haloalkyl, $C_1$-$C_6$ alkoxyalkyl, $C_2$-$C_6$ alkylcarbonyl, phenyl or benzyl wherein each of the phenyl or the benzyl may be optionally substituted with 1-3 $R^5$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^5$, biphenyl or naphthyl optionally substituted with 1-3 $R^5$;
$R^{10}$ is H, $C_1$-$C_6$ alkyl, $C_1$-$C_6$ haloalkyl, $C_1$-$C_6$ alkoxyalkyl, $C_2$-$C_6$ alkylcarbonyl, or benzyl, wherein the benzyl may be optionally substituted with 1-3 $R^5$;
alternatively $R^9$ and $R^{10}$ may be taken together to form a 5- or 6-membered saturated or unsaturated ring containing 1-3 heteroatoms wherein each ring may be optionally substituted with 1-3 $R^5$;
$R^{11}$ is H or $C_1$-$C_4$ alkyl;
$R^{12}$ is H, cyano, hydroxyl, $C_1$-$C_4$ alkyl, $C_1$-$C_6$ alkoxy, $C_2$-$C_6$ alkylcarbonyl, phenyl or benzyl wherein each of the phenyl or the benzyl may be optionally substituted with 1-3 $R^5$;
alternatively $R^{11}$ and $R^{12}$ may be taken together to form a 5- or 6-membered saturated or unsaturated ring containing 1-3 heteroatoms wherein each ring may be optionally substituted with 1-3 $R^5$;
$R^{13}$ is H, $C_1$-$C_4$ alkyl, $C_1$-$C_6$ alkoxy, $C_2$-$C_6$, alkylcarbonyl, phenyl or benzyl wherein each of the phenyl or the benzyl may be optionally substituted with 1-3 $R^5$;
alternatively $R^{12}$ and $R^{13}$ may be taken together to form a 5- or 6-membered saturated or unsaturated ring containing 1-3 hetero atoms wherein each ring may be optionally substituted with 1-3 $R^5$; and
$R^{14}$ is $C_1$-$C_6$ alkyl, $C_1$-$C_6$ haloalkyl, amino, $C_1$-$C_6$ alkylamino, $C_2$-$C_6$ dialkylamino, a phenyl or benzyl wherein each of the phenyl or the benzyl may be optionally substituted with 1-3 $R^5$, 4-(3-chloro-5-(trifluoromethyl)pyridin-2-yloxy)-3-methylphenyl, 4-(3-chloro-5-(trifluoromethyl)pyridin-2-yloxy)-2-methylphenyl, or a 5- or 6-membered saturated or unsaturated ring containing 1-3 heteroatoms wherein each ring may be optionally substituted with 1-3 $R^5$.

Another embodiment of the present disclosure may include a fungicidal composition for the control or prevention of fungal attack comprising the compounds described below and a phytologically acceptable carrier material.

Yet another embodiment of the present disclosure may include a method for the control or prevention of fungal attack on a plant, the method including the steps of applying a fungicidally effective amount of one or more of the compounds described below to at least one of the fungus, the plant, an area adjacent to the plant, and the seed adapted to produce the plant.

The term "alkyl" refers to a branched, unbranched, or cyclic carbon chain, including methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including ethenyl, propenyl, butenyl, isopropenyl, isobutenyl, cyclohexenyl, and the like.

The term "alkynyl" refers to a branched or unbranched carbon chain containing one or more triple bonds including propynyl, butynyl and the like.

As used throughout this specification, the term 'R' refers to the group consisting of $C_{2-8}$ alkyl, $C_{3-8}$ alkenyl or $C_{3-8}$ alkynyl, unless stated otherwise.

The term "alkoxy" refers to an —OR substituent.

The term "alkoxycarbonyl" refers to a —C(O)—OR substituent.

The term "alkylcarbonyl" refers to a —C(O)—R substituent.

The term "alkylsulfonyl" refers to an —SO$_2$—R substituent.

The term "haloalkylsulfonyl" refers to an —SO$_2$—R substituent where R is fully or partially substituted with Cl, F, I, or Br or any combination thereof.

The term "alkylthio" refers to an —S—R substituent.

The term "halothio" refers to a sulfur substituted with three or five F substituents.

The term "haloalkylthio" refers to an alkylthio, which is substituted with Cl, F, I, or Br or any combination thereof.

The term "alkylaminocarbonyl" refers to a —C(O)—N(H)—R substituent.

The term "dialkylaminocarbonyl" refers to a —C(O)—NR$_2$ substituent.

The term "alkylcycloalkylamino" refers to a cycloalkylamino substituent that is substituted with an alkyl group.

The term "trialkylsilyl" refers to —SiR$_3$.

The term "cyano" refers to a —C≡N substituent.

The term "hydroxyl" refers to an —OH substituent.

The term "amino" refers to a —NH$_2$ substituent.

The term "alkylamino" refers to a —N(H)—R substituent.

The term "dialkylamino" refers to a —NR$_2$ substituent.

The term "alkoxyalkoxy" refers to —O(CH$_2$)$_n$O(CH$_2$)$_m$CH$_3$ where n is 1-3 and m is 0-2.

The term "alkoxyalkyl" refers to an alkoxy substitution on an alkyl.

The term "haloalkoxyalkyl" refers to an alkoxy substitution on an alkyl which is fully or partially substituted with Cl, F, Br, or I, or any combination thereof.

The term "hydroxyalkyl" refers to an alkyl which is substituted with a hydroxyl group.

The term "haloalkoxy" refers to an —OR—X substituent, wherein X is Cl, F, Br, or I, or any combination thereof.

The term "haloalkyl" refers to an alkyl, which is substituted with Cl, F, I, or Br or any combination thereof.

The term "haloalkenyl" refers to an alkenyl, which is substituted with Cl, F, I, or Br or any combination thereof.

The term "haloalkynyl" refers to an alkynyl which is substituted with Cl, F, I, or Br or any combination thereof.

The term "halogen" or "halo" refers to one or more halogen atoms, defined as F, Cl, Br, and I.

The term "hydroxycarbonyl" refers to a —C(O)—OH substituent.

The term "nitro" refers to a —NO$_2$ substituent.

The term "aryl" refers to a cyclic, aromatic substituent consisting of hydrogen and carbon.

Throughout the disclosure, reference to the compounds of Formula I is read as also including optical isomers and salts of Formula I, and hydrates thereof. Specifically, when Formula I contains a branched chain alkyl group, it is understood that such compounds include optical isomers and racemates thereof. Exemplary salts include: hydrochloride, hydrobromide, hydroiodide, and the like. Additionally, the compounds of Formula I may include tautomeric forms.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric and tautomeric forms of the molecule.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or seeds.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

Additional features and advantages of the present invention will become apparent to those skilled in the art upon consideration of the following detailed description of the illustrative embodiments exemplifying the best mode of carrying out the invention as presently perceived.

DETAILED DESCRIPTION OF THE DISCLOSURE

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants. The materials may be applied in the form of any of the generally used formulation types, for example, as solutions, dusts, wettable powders, flowable concentrates, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water suspendable, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water dispersible granules, comprise an intimate mixture of one or more of the compounds of Formula 1, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 10 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 5 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines and blends of surfactants with mineral or vegetable oils. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula 1 and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzylaminobenzenesulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquation, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, laminarin, kasugamycin, kasugamycin hydrochloride hydrate, kresoxim-methyl, mancopper, mancozeb, mandipropamid, maneb, mepanipyrim, mepronil, mercuric chloride, mercuric oxide, mercurous chloride, metalaxyl, mefenoxam, meptyldinocap, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila*, *Fusarium oxysporum*, *Gliocladium* spp., *Phlebiopsis gigantea*, *Streptomyces griseoviridis*, *Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury)sulfate, bis(tributyltin)oxide, buthiobate, cadmium calcium copper zinc chromate sulfate, carbamorph, CECA, chlobenthiazone, chloraniformethan, chlorfenazole, chlorquinox, climbazole, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, 5-fluorocytosine and profungicides thereof, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3- nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, picolinamide UK-2A and derivatives thereof, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, and zarilamide, and any combinations thereof.

Additionally, the compounds of the present invention may be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad and spinetoram; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dessicant insecticides such as boric acid, diatomaceous earth and silica gel; diamide insecticides such as chlorantraniliprole, cyantraniliprole and flubendiamide; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethyl-amine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, alpha-endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, isofenphos-methyl, methamidophos and propetamphos; phosphorodiamide insecticides such as dimefox, mazidox, mipafox and schradan; oxadiazine insecticides such as indoxacarb; oxadiazoline insecticides such as metoxadiazone; phthalimide insecticides such as dialifos, phosmet and tetramethrin; pyrazole insecticides such as tebufenpyrad, tolefenpyrad; phenylpyrazole insecticides such as acetoprole, ethiprole, fipronil, pyrafluprole, pyriprole and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, meperfluthrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tetramethylfluthrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetramic acid insecticides such as spirotetramat; tetronic acid insecticides such as spiromesifen; thiourea insecticides such as diafenthiuron; urea insecticides such as flucofuron and sulcofuron; and unclassified insecticides such as closantel, copper naphthenate, crotamiton, EXD, fenazaflor, fenoxacrim, hydramethylnon, isoprothiolane, malonoben, metaflumizone, nifluridide, plifenate, pyridaben, pyridalyl, pyrifluquinazon, rafoxanide, sulfoxaflor, triarathene and triazamate, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: amide herbicides such as allidochlor, beflubutamid, benzadox, benzipram, bromobutide, cafenstrole, CDEA, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; thioamide herbicides such as chlorthiamid; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; benzothiazole herbicides such as benzazolin; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glufosinate-P, glyphosate and piperophos; phenoxy herbicides such as bromofenoxim, clomeprop, 2,4-DEB, 2,4-DEP, difenopenten, disul, erbon, etnipromid, fenteracol and trifopsime; oxadiazoline herbicides such as methazole, oxadiargyl, oxadiazon; oxazole herbicides such as fenoxasulfone; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazole herbicides such as pyroxasulfone; benzoylpyrazole herbicides such as benzofenap, pyrasulfotole, pyrazolynate, pyrazoxyfen, and topramezone; phenylpyrazole herbicides such as fluazolate, nipyraclofen, pioxaden and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, pro sulfocarb, pyributicarb, sulfallate, thiobencarb, tiocarbazil, triallate and vernolate; thiocarbonate herbicides such as dimexano, EXD and proxan; thiourea herbicides such as methiuron; triazine herbicides such as dipropetryn, indaziflam, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; iriazolone herbicides such as amicarbazone, bencarbazone, carfentrazone, flucarbazone, ipfencarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as benzfendizone, bromacil, butafenacil, flupropacil, isocil, lenacil, saflufenacil and terbacil; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, nicosulfuron, orthosulfamuron, oxasulfuron, primisulfuron, propyrisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; ihiadiazolylurea herbicides such as buthiuron, ethidimuron, tebuthiuron, thiazafluron and thidiazuron; and unclassified herbicides such as acrolein, allyl alcohol, aminocyclopyrachlor, azafenidin, bentazone, benzobicyclon, bicyclopyrone, buthidazole, calcium cyanamide, cambendichlor, chlorfenac, chlorfenprop, chlorflurazole, chlorflurenol, cinmethylin, clomazone, CPMF, cresol, cyanamide, orthodichlorobenzene, dimepiperate, endothal, fluoromidine, fluridone, flurochloridone, flurtamone, fluthiacet, indanofan, methyl isothiocyanate, OCH, oxaziclomefone, pentachlorophenol, pentoxazone, phenylmercury acetate, pro sulfalin, pyribenzoxim, pyriftalid, quinoclamine, rhodethanil, sulglycapin, thidiazimin, tridiphane, trimeturon, tripropindan and tritac.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants. Additional benefits may include, but are not limited to, improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, wheat leaf blotch (*Septoria tritici*, also known as *Mycosphaerella graminicola*), apple scab (*Venturia inaequalis*), and *Cercospora* leaf spots of sugar beets (*Cercospora heticola*), leaf spots of peanut (*Cercospora arachidicola* and *Cercosporidium personatum*) and other crops, and black sigatoka of bananas (*Mycosphaerella fujiensis*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact amount of a compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, g/m²).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

The following examples are presented to illustrate the various aspects of the compounds of the present disclosure and should not be construed as limitations to the claims.

Example 1

Preparation of N'-(1-benzenesulfonyl-5-fluoro-2-oxo-1,2-dihydro-pyrimidin-4-yl)-N,N-dimethylformamidine (1)

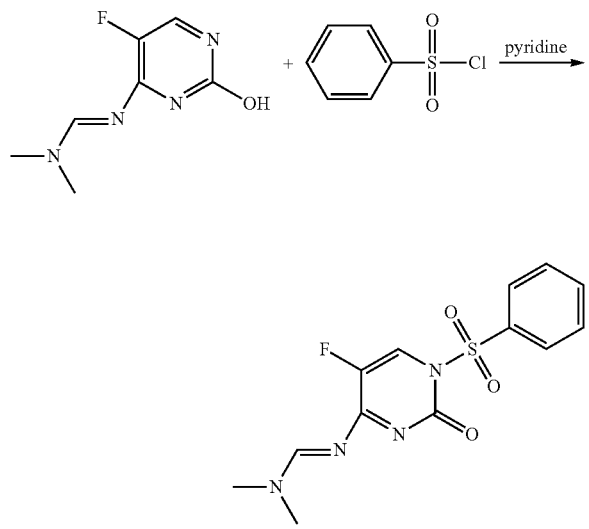

To an 8 mL screw-cap vial were added pyridine (2 mL), N'-(5-fluoro-2-hydroxy-pyrimidin-4-yl)-N,N-dimethylformamidine (100 mg, 0.54 mmol), and benzenesulfonyl chloride (106 mg, 0.60 mmol), and the mixture was shaken at room temperature for 24 hours (h). The crude mixture was partitioned between ethyl acetate (EtOAc) and saturated aqueous sodium bicarbonate (satd aq $NaHCO_3$), and the organic phase was dried over magnesium sulfate ($MgSO_4$), filtered, and evaporated to yield 153 mg of crude material. Reverse phase chromatography furnished the title product as a white solid (33 mg, 19%): mp 203-204° C.; $^1$H NMR (300 MHz, $CDCl_3$) δ 8.77 (s, 1H), 8.16-8.11 (m, 3H), 7.72-7.65 (m, 1H), 7.60-7.53 (m, 2H), 3.24 (s, 3H), 3.23 (s, 3H); ESIMS m/z 325 ([M+H]$^+$).

Example 2

Preparation of N'-[1-(4-chloro-benzenesulfonyl)-5-fluoro-2-oxo-1,2-dihydro-pyrimidin-4-yl]-N,N-dimethylformamidine (2)

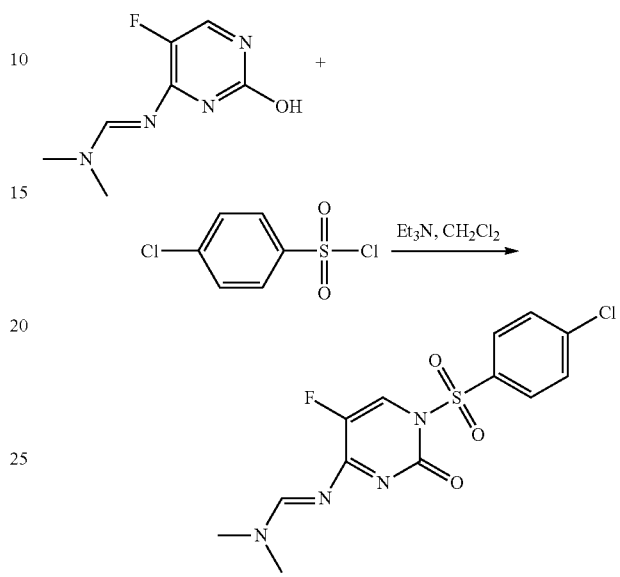

To a 25 mL screw-cap vial were added dichloromethane ($CH_2Cl_2$; 10 mL), N'-(5-fluoro-2-hydroxy-pyrimidin-4-yl)-N,N-dimethylformamidine (250 mg, 1.36 mmol), and triethylamine ($Et_3N$, 300 mg, 3 mmol). To this mixture was added 4-chlorobenzenesulfonyl chloride (315 mg, 1.5 mmol), and the resulting mixture was shaken at room temperature for 3 h. The crude reaction mixture was partitioned between $CH_2Cl_2$ and brine, dried over $MgSO_4$, filtered, and evaporated. The residue was purified by reverse phase chromatography to yield the title compound as a white solid (321 mg, 66%): mp 207-210° C.; $^1$H NMR (300 MHz, $CDCl_3$) δ 8.75 (s, 1H), 8.08-8.02 (m, 3H), 7.53-7.47 (m, 2H), 3.23 (s, 3H), 3.21 (s, 3H); ESIMS m/z 360 ([M+H]$^+$).

Compounds 3-7 in Table I were synthesized as in Example 2.

Example 3

Preparation of 4-amino-1-(4-chloro-benzenesulfonyl)-5-fluoro-1H-pyrimidin-2-one (8; Method A)

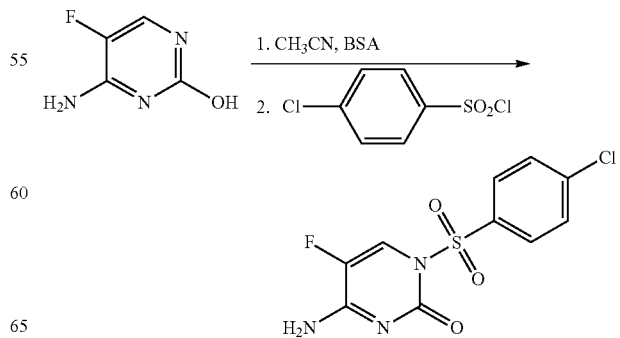

To 4-amino-5-fluoro-pyrimidin-2-ol* (1.0 g, 7.75 mmol) in acetonitrile (CH$_3$CN; 40 mL) was added bis-N,O-trimethylsilylacetamide (BSA; 5.7 mL, 23.3 mmol) and the mixture was heated to 70° C. for 1 h resulting in a clear solution. After cooling to room temperature, 4-chlorobenzene sulfonyl chloride (1.8 g, 8.5 mmol) was added, and the mixture was stirred for 24 h. The solvent was evaporated and the residue was partitioned between EtOAc and brine. The organic phase was dried over MgSO$_4$, filtered, and evaporated to yield the crude product as a white solid (1.3 g). Recrystallization from EtOAc and heptane furnished the title product as a white solid (0.96 g, 41%): mp 174-178° C.; $^1$H NMR (300 MHz, CDCl$_3$) δ 8.5 (br s, 1H), 8.08 (d, J=5.9 Hz, 1H), 8.04-7.98 (m, 2H), 7.55-7.49 (m, 2H), 5.9 (br s, 1H); ESIMS m/z 304 ([M+H]$^+$).

*4-Amino-5-fluoro-pyrimidin-2-ol can be purchased commercially.

Compounds 9-23 in Table I were synthesized as in Example 3.

Example 4

Preparation of 4-amino-1-(4-chloro-benzenesulfonyl)-5-fluoro-1H-pyrimidin-2-one (8; Method B)

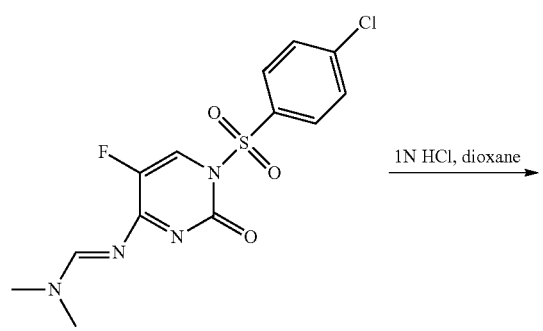

To an 8 mL screw-cap vial was added dioxane (9 mL), 1 N aqueous hydrochloric acid (HCl; 1 mL), and N'-[1-(4-chloro-benzenesulfonyl)-5-fluoro-2-oxo-1,2-dihydro-pyrimidin-4-yl]-N,N-dimethylformamidine (269 mg, 0.75 mmol). The mixture was shaken at room temperature for 16 h, evaporated under a stream of nitrogen, and partitioned between EtOAc and satd aq NaHCO$_3$. The organic phase was dried over MgSO$_4$, filtered, and evaporated to yield the title product as a white solid (196 mg, 86%): mp 174-178° C.; $^1$H NMR (300 MHz, CDCl$_3$) δ 8.5 (br s, 1H), 8.08 (d, J=5.9 Hz, 1H), 8.04-7.98 (m, 2H), 7.55-7.49 (m, 2H), 5.9 (br s, 1H); ESIMS m/z 304 ([M+H]$^+$).

Compounds 24-27 in Table I were synthesized as in Example 4.

Example 5

Preparation of N'-[5-fluoro-1-(1-methyl-1H-imidazole-4-sulfonyl)-2-oxo-1,2-dihydro-pyrimidin-4-yl]-N,N-dimethylformamidine (28)

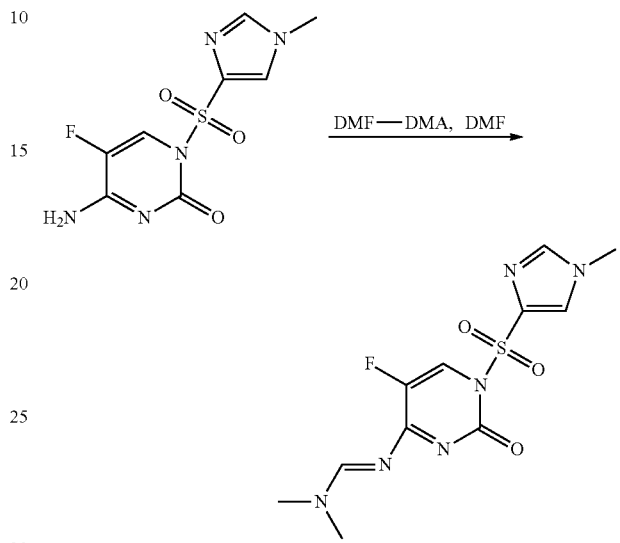

To an 8 mL screw-cap vial was added 4-amino-5-fluoro-1-(1-methyl-1H-imidazole-4-sulfonyl)-1H-pyrimidin-2-one (80 mg, 0.3 mmol), N,N-dimethylformamide (DMF; 3 mL), and dimethylformamide dimethylacetal (DMF-DMA; 70 mg, 0.6 mmol). The mixture was shaken at room temperature for 16 h, diluted with Et$_2$O and filtered to yield the title product as a light yellow solid (68 mg, 69%): mp 228-232° C. dec; $^1$H NMR (300 MHz, DMSO-d$_6$) δ 8.67 (s, 1H), 8.25-8.21 (m, 2H), 7.82 (s, 1H), 3.73 (s, 3H), 3.24 (s, 3H), 3.13 (s, 3H); ESIMS m/z 329 ([M+H]$^+$).

Compounds 29-32 in Table I were synthesized as in Example 5.

Example 6

Preparation of N-(1-benzenesulfonyl-5-fluoro-2-oxo-1,2-dihydro-pyrimidin-4-yl)-benzamide (33)

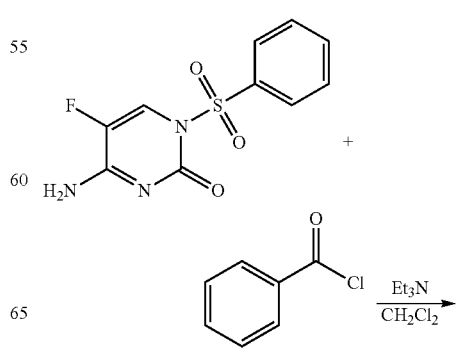

-continued

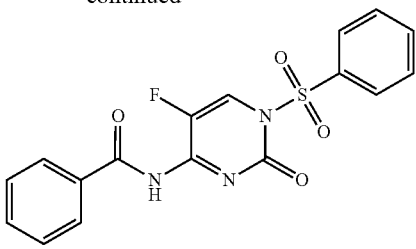

To an 8 mL screw-cap vial was added 4-amino-1-benzenesulfonyl-5-fluoro-1H-pyrimidin-2-one (200 mg, 0.74 mmol), $CH_2Cl_2$ (5 mL), $Et_3N$ (200 mg, 1.98 mmol), and benzoyl chloride (114 mg, 0.82 mmol). The mixture was shaken at room temperature for 2.5 h, evaporated under a stream of nitrogen, and partitioned between EtOAc and $H_2O$. The organic phase was dried over $MgSO_4$, filtered, and evaporated. The crude material was partially purified by normal phase chromatography (gradient, 10 to 50% EtOAc/petroleum ether), and fractions containing the major product were evaporated and recrystallized from EtOAc and petroleum ether to yield the title product as a white solid (112 mg, 41%): mp 150-151° C.; $^1$H NMR (300 MHz, $CDCl_3$) δ 8.31-8.25 (m, 2H), 8.24 (d, J=5.8 Hz, 1H), 8.16-8.11 (m, 2H), 7.82-7.75 (m, 1H), 7.68-7.56 (m, 3H), 7.52-7.44 (m, 2H); ESIMS m/z 374 ([M+H]$^+$), 372 ([M−H]$^−$).

Compounds 34-37 in Table I were synthesized as in Example 6.

Example 7

Preparation of 4-chloro-N-[1-(4-chlorobenzenesulfonyl)-5-fluoro-2-oxo-1,2-dihydropyrimidin-4-yl]benzamideamide (38)

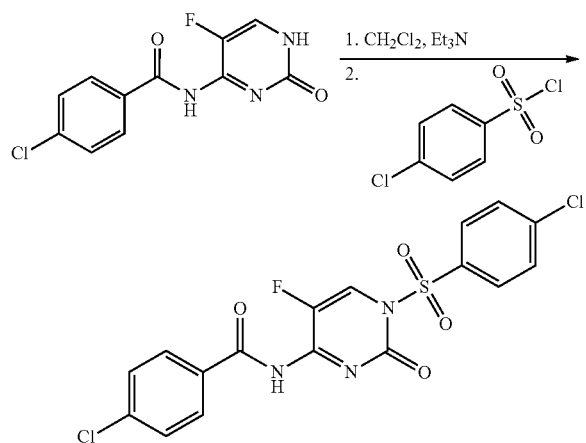

To a suspension of 4-chloro-N-(5-fluoro-2-oxo-1,2-dihydropyrimid-4-yl)benzamide (0.10 g, 0.37 mmol) in $CH_2Cl_2$ (4 mL) were added $Et_3N$ (0.08 g, 0.82 mmol) and 4-chlorobenzenesulfonyl chloride (0.087 g, 0.41 mmol) at 0° C., and the resulting mixture was warmed to room temperature and stirred for 3 h. The reaction was diluted with $CH_2Cl_2$ (10 mL) and washed with brine. The phases were separated and the organic phase was dried over sodium sulfate ($Na_2SO_4$), filtered, and concentrated to an amber oil (0.295 g). Purification by normal phase chromatography (12 g $SiO_2$; gradient, 0 to 35% EtOAc/hexanes) afforded 4-chloro-N-[1-(4-chlorobenzenesulfonyl)-5-fluoro-2-oxo-1,2-dihydropyrimidin-4-yl]benzamide (0.025 g, 26%) as a white solid: mp 169-172° C.; $^1$H NMR (300 MHz, $CDCl_3$) δ 12.59 (s, 1H), 8.29-8.15 (m, 3H), 8.05 (d, J=8.8 Hz, 2H), 7.59 (d, J=8.7 Hz, 2H), 7.42 (d, J=8.6 Hz, 2H); ESIMS m/z 442 ([M+H]$^+$), 440 ([M−H]$^−$).

Compound 39 in Table I was synthesized as in Example 7.

Example 8

Preparation of 1-(1-benzenesulfonyl-5-fluoro-2-oxo-1,2-dihydropyrimidin-4-yl)-3-phenylurea (40)

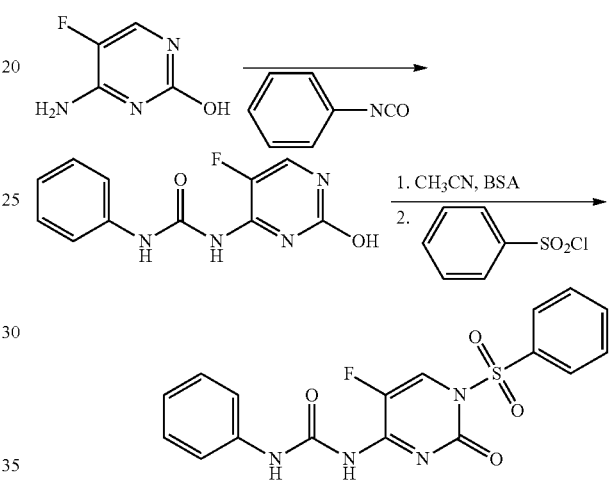

A) To a suspension of 4-amino-5-fluoropyrimidin-2-ol (0.200 g, 1.5 mmol) in anhydrous DMF (3 mL) was added phenylisocyanate (0.251 g, 2.1 mmol) and the mixture was stirred at 23° C. for 1 h and then at 60° C. for 16 h. The reaction mixture was cooled to room temperature, and the residual solid was collected by filtration. The filter cake was washed with diethyl ether ($Et_2O$) and dried in a vacuum oven at 40° C. for 3 h to give 1-(5-fluoro-2-hydroxypyrimidin-4-yl)-3-phenylurea as a white solid (0.210 g, 55%), which was used immediately in the next step.

B) To a suspension of 1-(5-fluoro-2-hydroxypyrimidin-4-yl)-3-phenylurea (0.200 g, 0.8 mmol) in anhydrous $CH_3CN$ (4 mL) was added BSA (0.487 g, 2.4 mmol), and the mixture was warmed to 70° C. and stirred for 1 h. The resulting solution was cooled to room temperature, treated with benzenesulfonyl chloride (0.156 g, 0.9 mmol), and the mixture was stirred for 12 h. The solvent was evaporated, and the residue was partitioned between EtOAc and brine. The organic phase was dried over $MgSO_4$, filtered, and concentrated to give the crude product as a white solid. Recrystallization from EtOAc and heptane afforded 1-(1-benzenesulfonyl-5-fluoro-2-oxo-1,2-dihydropyrimidin-4-yl)-3-phenylurea as a white solid (0.100 g, 32%): mp 210-214° C.; $^1$H NMR (400 MHz, DMSO-$d_6$) δ 11.26 (dd, J=3.7, 1.1 Hz, 1H), 10.87 (m, 1H), 8.65 (m, 1H), 8.10 (d, J=7.5 Hz, 2H), 7.85 (t, J=7.5 Hz, 1H), 7.71 (m, 2H), 7.45 (m, 2H), 7.34 (m, 2H), 7.10 (m, 1H); ESIMS m/z 389 ([M+H]$^+$).

Compounds 41-43 in Table I were synthesized as in Example 8.

Example 9

Preparation of (1-benzenesulfonyl-5-fluoro-2-oxo-1,2-dihydropyrimidin-4-yl)-3-phenylthiourea (44)

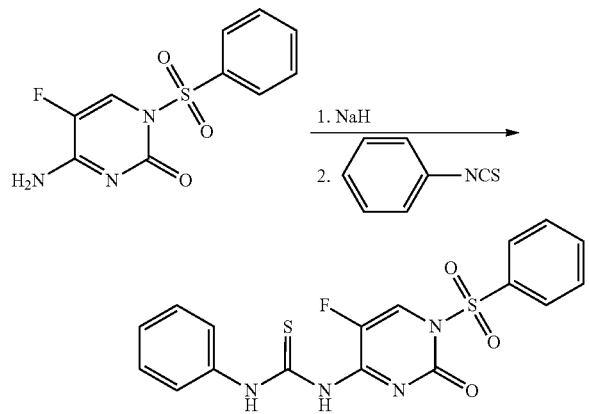

Example 10

Preparation of (1-benzenesulfonyl-5-fluoro-2-oxo-1,2-dihydropyrimidin-4-yl)carbamic acid phenyl ester (47)

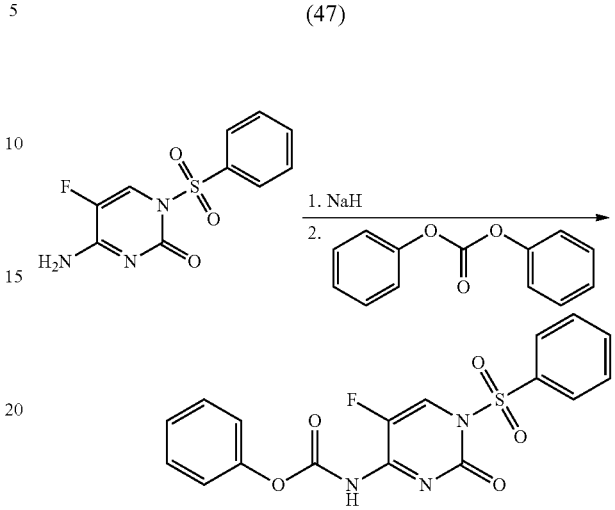

To a suspension of 4-amino-1-benzenesulfonyl-5-fluoro-1H-pyrimidin-2-one (0.20 g, 0.74 mmol) in anhydrous tetrahydrofuran (THF; 3 mL) was added sodium hydride (NaH; 0.044 g of 60 wt % suspension in mineral oil, 1.11 mmol) at 0° C. After gas evolution had subsided, the mixture was transferred via cannula to an ice-cold mixture of phenyl isothiocyanate (1.0 g, 7.4 mmol) in anhydrous THF (5 mL) and stirred for 6 h. The reaction mixture was diluted with EtOAc (25 mL), and the resulting solution was washed with satd aq ammonium chloride (NH$_4$Cl; 15 mL) and brine (15 mL). The organic phase was dried over Na$_2$SO$_4$, filtered, and the solvent evaporated. The residue was purified by precipitation from methanol (MeOH) and Et$_2$O to give (1-benzenesulfonyl-5-fluoro-2-oxo-1,2-dihydropyrimidin-4-yl)-3-phenylthiourea as a light yellow solid (0.025 g, 8%): mp 205-208° C.; $^1$H NMR (400 MHz, DMSO-d$_6$) δ 11.26 (dd, J=3.7, 1.1 Hz, 1H), 10.87 (m, 1H), 8.65 (m, 1H), 8.10 (d, J=7.5 Hz, 2H), 7.85 (t, J=7.5 Hz, 1H), 7.71 (m, 2H), 7.45 (m, 2H), 7.34 (m, 2H), 7.10 (m, 1H); ESIMS m/z 405 ([M+H]$^+$).

Compounds 45 and 46 in Table I were synthesized as in Example 9.

To a suspension of 4-amino-1-benzenesulfonyl-5-fluoro-1H-pyrimidin-2-one (0.20 g, 0.74 mmol) in anhydrous THF (3 mL) was added NaH (0.044 g of 60 wt % suspension in mineral oil, 1.11 mmol) at 0° C. After gas evolution had subsided, the mixture was transferred via cannula to an ice-cold mixture of diphenyl carbonate (1.5 g, 7.4 mmol) in anhydrous THF (5 mL) and stirred for 6 h. The reaction was diluted with EtOAc (25 mL) and the resulting solution was washed with satd aq NH$_4$Cl (15 mL) and brine (15 mL). The organic phase was dried over Na$_2$SO$_4$, filtered, and the solvent evaporated. The residue was purified by precipitation from MeOH and Et$_2$O to give (1-benzenesulfonyl-5-fluoro-2-oxo-1,2-dihydropyrimidin-4-yl)carbamic acid phenyl ester as a light brown solid (0.070 g, 24%): mp 182-185° C.; $^1$H NMR (400 MHz, DMSO-d$_6$) δ 7.95 (m, 2H), 7.87 (d, J=7.0 Hz, 1H), 7.71 (d, J=7.5 Hz, 1H), 7.61 (t, J=7.7 Hz, 2H), 7.33 (t, J=7.9 Hz, 2H), 7.15 (d, J=7.3 Hz, 1H), 7.06 (d, J=7.6 Hz, 2H); ESIMS m/z 390 ([M+H]$^+$), 388 ([M−H]$^−$).

Compounds 48-50 in Table 1 were synthesized as in Example 10.

TABLE I

Compounds and Related Characterization Data

| Cmpd | Structure | MS | mp (° C.) | Appearance | $^1$H NMR* (δ, CDCl$_3$) |
|---|---|---|---|---|---|
| 3 | ![structure] | ESIMS m/z 263 ([M + H]$^+$) | 133-134 | white crystalline solid | 8.8 (s, 1H), 7.81 (d, 1H), 3.6 (s, 3H), 3.23 (s, 3H), 3.21 (s, 3H) |

TABLE I-continued

Compounds and Related Characterization Data

| Cmpd | Structure | MS | mp (° C.) | Appearance | $^1$H NMR* (δ, CDCl$_3$) |
|---|---|---|---|---|---|
| 4 | 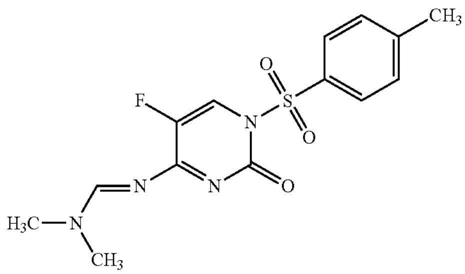 | ESIMS m/z 340 ([M + H]$^+$) | 199-203 | white solid | 8.73 (s, 1H), 8.09 (d, J = 5.6 Hz, 1H), 7.98 (d, J = 8.4 Hz, 2H), 7.32 (d, J = 8.4 Hz, 2H), 3.21 (s, 3H), 3.20 (s, 3H), 2.42 (s, 3H) |
| 5 | 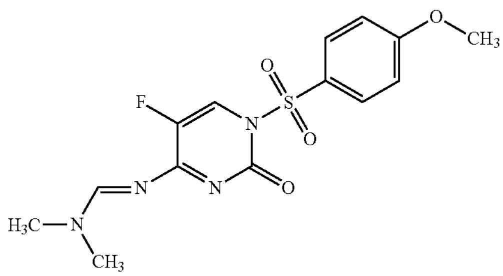 | ESIMS m/z 356 ([M + H]$^+$) | 188-190 | white solid | 8.67 (s, 1H), 8.04 (d, J = 5.6 Hz, 1H), 7.99 (d, J = 9.2 Hz, 2H), 6.92 (d, J = 9.2 Hz, 2H), 3.81 (s, 3H), 3.16 (s, 6H) |
| 6 | 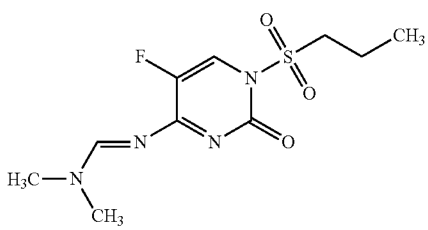 [SMILES: CCCS(=O)(=O)n1cc(F)c(/N=C/N(C)C)nc1=O] | ESIMS m/z 291 ([M + H]$^+$) | 144-145 | yellow-orange solid | 8.83 (s, 1H), 7.84 (d, J = 5.6 Hz, 1H), 3.84-3.77 (m, 2H), 3.25 (s, 3H), 3.24 (s, 3H), 1.91-1.74 (m, 2H), 1.04 (t, J = 7.6 Hz, 3H) |
| 7 | 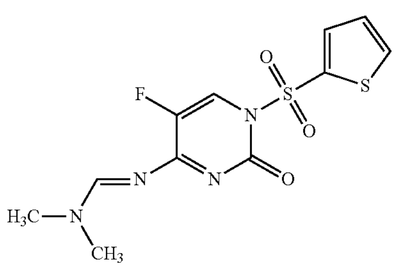 [SMILES: CN(C)/C=N/c1nc(=O)n(S(=O)(=O)c2cccs2)cc1F] | ESIMS m/z 331 ([M + H]$^+$) | 205-207 | tan solid | 8.79 (s, 1H), 8.09-8.06 (m, 1H), 8.04 (d, J = 5.6 Hz, 1H), 7.77-7.74 (m, 1H), 7.15-7.11 (m, 1H), 3.23 (s, 6H) |
| 9 | 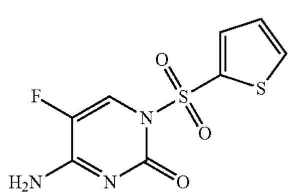 [SMILES: Nc1nc(=O)n(S(=O)(=O)c2cccs2)cc1F] | ESIMS m/z 275 ([M + H]$^+$) | 187-189 | white solid | (DMSO-d$_6$) 8.59 (br s, 1H), 8.33-8.24 (br s and d, 2H), 8.21-8.18 (m, 1H), 8.00-7.96 (m, 1H), 7.29-7.24 (m, 1H) |
| 10 | 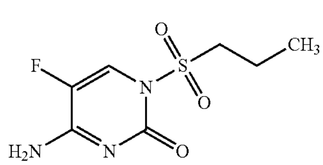 | ESIMS m/z 236 ([M + H]$^+$) | 144-146 | white solid | (DMSO-d$_6$) 8.58 (br s, 1H), 8.28 (br s, 1H), 8.01 (d, J = 6.6 Hz, 1H), 3.88-3.82 (m, 2H), 1.74-1.63 (m, 2H), 0.97 (t, J = 7.4 Hz, 3H) |

TABLE I-continued

Compounds and Related Characterization Data

| Cmpd | Structure | MS | mp (° C.) | Appearance | $^1$H NMR* (δ, CDCl$_3$) |
|---|---|---|---|---|---|
| 11 | 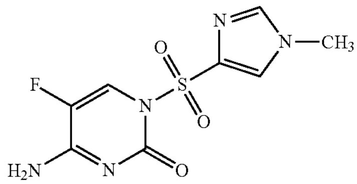 [SMILES: Cn1cnc(S(=O)(=O)n2cc(F)c(N)nc2=O)c1] | ESIMS m/z 274 ([M + H]$^+$) | 235-237 | white solid | (DMSO-d$_6$) 8.48 (br s, 1H), 8.23 (d, J = 6.6 Hz, 1H), 8.21 (br s, 1H), 8.20 (s, 1H), 7.84 (s, 1H), 3.74 (s, 3H) |
| 12 | 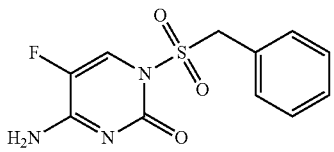 [SMILES: Nc1nc(=O)n(S(=O)(=O)Cc2ccccc2)cc1F] | ESIMS m/z 284 ([M + H]$^+$) | 172-174 | white solid | (DMSO-d$_6$) 8.57 (br s, 1H), 8.25 (br s, 1H), 7.65 (d, J = 6.6 Hz, 1H), 7.41-7.35 (m, 3H), 7.30-7.26 (m, 2H), 5.20 (s, 2H) |
| 13 | 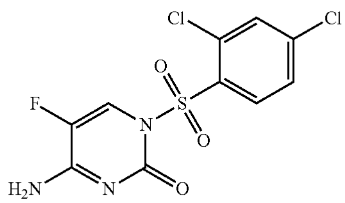 [SMILES: Nc1nc(=O)n(S(=O)(=O)c2ccc(Cl)cc2Cl)cc1F] | ESIMS m/z 339 ([M + H]$^+$) | 229-230 | white solid | (DMSO-d$_6$) 8.56 (br s, 2H), 8.30 (d, J = 6.3 Hz, 1H), 8.17 (d, J = 8.6 Hz, 1H), 7.95 (d, J = 2.0 Hz, 1H), 7.74 (dd, J = 8.6, 2.0 Hz, 1H) |
| 14 | 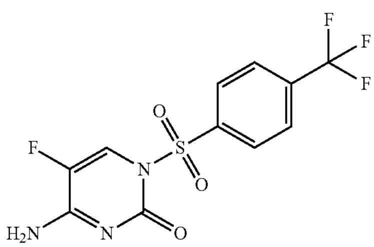 [SMILES: Nc1nc(=O)n(S(=O)(=O)c2ccc(C(F)(F)F)cc2)cc1F] | ESIMS m/z 338 ([M + H]$^+$) | 202-204 | white solid | (DMSO-d$_6$) 8.66 (br s, 1H), 8.37 (br s, 1H), 8.33 (d, J = 6.6 Hz, 1H), 8.25 (d, J = 8.5 Hz, 2H), 8.06 (d, J = 8.5 Hz, 2H) |
| 15 | 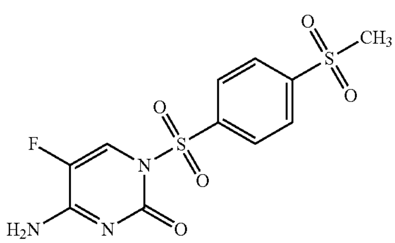 [SMILES: CS(=O)(=O)c1ccc(S(=O)(=O)n2cc(F)c(N)nc2=O)cc1] | ESIMS m/z 348 ([M + H]$^+$) | 220-223 | white solid | (DMSO-d$_6$ + CD$_3$CO$_2$D) 8.30 (d, J = 6.6 Hz, 1H), 8.27-8.23 (m, 2H), 8.19-8.15 (m, 2H), 3.3 (s, 3H) |
| 16 | 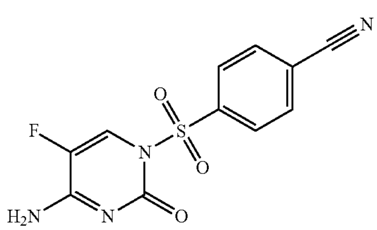 [SMILES: N#Cc1ccc(S(=O)(=O)n2cc(F)c(N)nc2=O)cc1] | ESIMS m/z 295 ([M + H]$^+$) | 210 | white solid | (DMSO-d$_6$) 8.67 (br s, 1H), 8.38 (br s, 1H), 8.30 (d, J = 6.6 Hz, 1H), 8.22-8.13 (m, 4H) |
| 17 | 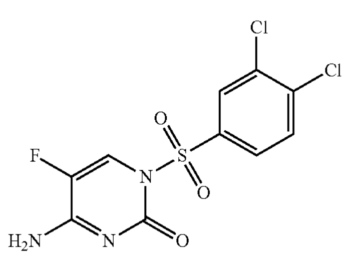 [SMILES: Nc1nc(=O)n(S(=O)(=O)c2ccc(Cl)c(Cl)c2)cc1F] | ESIMS m/z 338 ([M + H]$^+$) | 206-207 | white solid | (DMSO-d$_6$) 8.65 (br s, 1H), 8.36 (br s, 1H), 8.28 (d, J = 2 Hz, 1H), 8.26 (d, J = 6.6 Hz, 1H), 8.01 (dd, J = 8.6, 2 Hz, 1H), 7.96 (d, J = 8.6 Hz, 1H) |

TABLE I-continued

Compounds and Related Characterization Data

| Cmpd | Structure | MS | mp (° C.) | Appearance | $^1$H NMR* (δ, CDCl$_3$) |
|---|---|---|---|---|---|
| 18 | 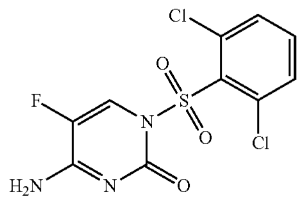 [SMILES: Nc1nc(=O)n(S(=O)(=O)c2c(Cl)cccc2Cl)cc1F] | ESIMS m/z 338 ([M + H]$^+$) | 209-212 | off-white solid | (DMSO-d$_6$) 8.76 (s, 1H), 8.46 (s, 1H), 8.33 (d, J = 6.4 Hz, 1H), 7.70 (m, 3H) |
| 19 | 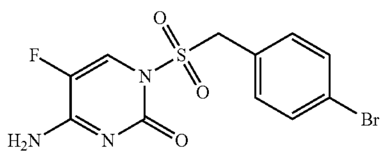 | ESIMS ESIMS m/z 361 ([M + H]$^+$) | 156-159 | white solid | (DMSO-d$_6$) 8.63 (s, 1H), 8.31 (s, 1H), 7.72 (d, J = 6.4 Hz, 1H), 7.63 (d, J = 8.4 Hz, 2H), 7.26 (d, J = 8.3 Hz, 2H), 5.23 (s, 2H) |
| 20 | 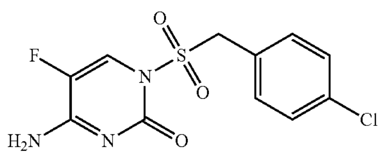 [SMILES: Nc1nc(=O)n(S(=O)(=O)Cc2ccc(Br)cc2)cc1F] | ESIMS m/z 318 ([M + H]$^+$) | 168-170 | white solid | (DMSO-d$_6$) 8.63 (s, 1H), 8.32 (s, 1H), 7.72 (d, J = 6.5 Hz, 1H), 7.49 (d, J = 8.5 Hz, 2H), 7.33 (d, J = 8.5 Hz, 2H), 5.25 (s, 2H) |
| 21 | 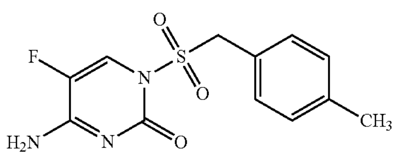 [SMILES: Cc1ccc(CS(=O)(=O)n2cc(F)c(N)nc2=O)cc1] | ESIMS m/z 298 ([M + H]$^+$) | 164-166 | white solid | (DMSO-d$_6$) 8.60 (s, 1H), 8.28 (s, 1H), 7.68 (d, J = 6.5 Hz, 1H), 7.19 (d, J = 3.0 Hz, 4H), 5.17 (s, 2H), 2.29 (s, 3H) |
| 22 | 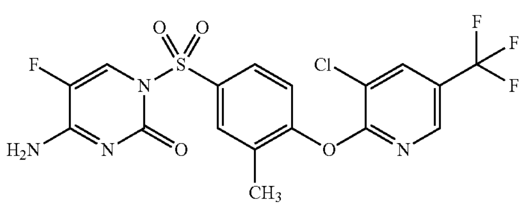 [SMILES: Cc1cc(S(=O)(=O)n2cc(F)c(N)nc2=O)ccc1Oc1ncc(C(F)(F)F)cc1Cl] | ESIMS m/z 480 ([M + H]$^+$) | | white solid | 9.12 (s, 1H), 8.26-8.20 (m, 1H), 8.07 (d, J = 6.5 Hz, 1H), 8.05-7.99 (m, 2H), 7.96 (dd, J = 8.6, 2.2 Hz, 1H), 7.31-7.23 (m, 1H), 6.21 (s, 1H), 2.26 (s, 3H) |
| 23 | 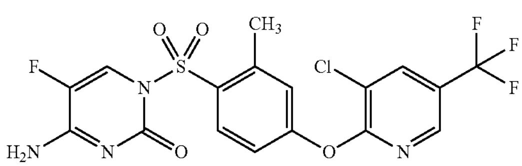 [SMILES: Cc1cc(Oc2ncc(C(F)(F)F)cc2Cl)ccc1S(=O)(=O)n1cc(F)c(N)nc1=O] | ESIMS m/z 481 ([M + 2H]$^+$), 477 ([M − 2H]$^-$) | 132 dec | white solid | (DMSO-d$_6$) 9.26 (s, 1H), 8.29 (d, J = 8.8 Hz, 2H), 8.11 (d, J = 5.8 Hz, 1H), 8.03 (d, J = 2.0 Hz, 1H), 7.22 (dd, J = 8.8, 2.3 Hz, 1H), 7.12 (d, J = 2.1 Hz, 1H), 6.24 (s, 1H), 2.51 (s, 3H) |
| 24 | 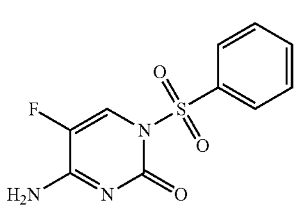 [SMILES: Nc1nc(=O)n(S(=O)(=O)c2ccccc2)cc1F] | ESIMS m/z 270 ([M + H]$^+$) | 195-196 | white solid | (CD$_3$CN) 8.17 (d, J = 6.3 Hz, 1H), 8.05-8.00 (m, 2H), 7.80-7.73 (m, 1H), 7.66-7.60) (m, 2H), 6.86 (br s, 1H), 6.62 (br s, 1H) |
| 25 | 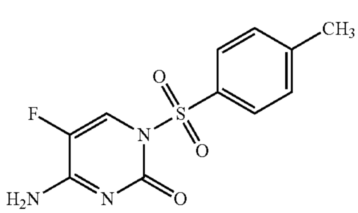 [SMILES: Cc1ccc(S(=O)(=O)n2cc(F)c(N)nc2=O)cc1] | ESIMS m/z 284 ([M + H]$^+$) | 208-210 | white solid | 8.18 (d, J = 6.3 Hz, 1H), 7.96-7.90 (m, 2H), 7.48-7.43 (m, 2H), 6.95 (br s, 1H), 6.64 (br s, 1H), 2.48 (s, 3H) |

TABLE I-continued

Compounds and Related Characterization Data

| Cmpd | Structure | MS | mp (° C.) | Appearance | $^1$H NMR* (δ, CDCl$_3$) |
|---|---|---|---|---|---|
| 26 | 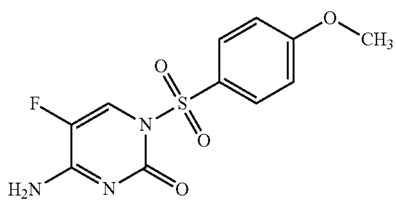 | ESIMS m/z 300 ([M + H]$^+$) | 182.5 | white solid | 8.40 (br s, 1H), 8.11 (d, J = 5.9 Hz, 1H), 8.04-7.98 (m, 2H), 7.02-6.96 (m, 2H), 5.77 (br s, 1H), 3.88 (s, 3H) |
| 27 | 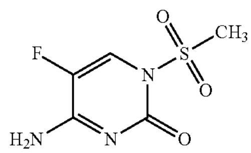 | ESIMS m/z 208 ([M + H]$^+$) | 181-184 | white solid | (CD$_3$CN) 7.91 (d, J = 6.3 Hz, 1H), 7.2 (br s, 1H), 6.7 (br s, 1H), 3.54 (s, 3H) |
| 29 | 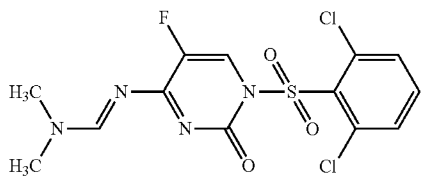 [SMILES: CN(C)/C=N/c1nc(=O)n(S(=O)(=O)c2c(Cl)cccc2Cl)cc1F] | ESIMS m/z 393 ([M + H]$^+$) | 207-211 | pale yellow solid | (DMSO-d$_6$) δ 8.73 (d, J = 0.6 Hz, 1H), 8.34 (d, J = 5.9 Hz, 1H), 7.72 (m, 3H), 3.28 (s, 3H), 3.17 (d, J = 0.8 Hz, 3H) |
| 30 | 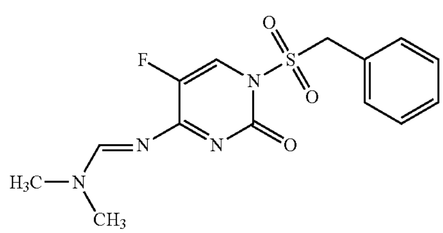 [SMILES: CN(C)/C=N/c1nc(=O)n(S(=O)(=O)Cc2ccccc2)cc1F] | ESIMS m/z 339 ([M + H]$^+$) | 152-154 | white solid | (DMSO-d$_6$) 8.82 (s, 1H), 7.68 (d, J = 6.0 Hz, 1H), 7.39 (m, 3H), 7.31 (dd, J = 6.6, 2.9 Hz, 2H), 5.26 (s, 2H), 3.31 (s, 3H), 3.15 (s, 3H) |
| 31 | 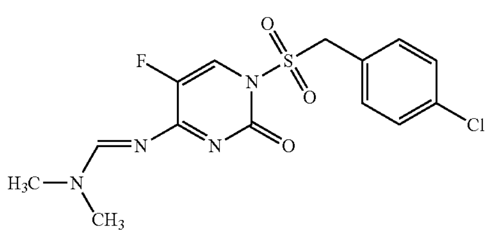 [SMILES: CN(C)/C=N/c1nc(=O)n(S(=O)(=O)Cc2ccc(Cl)cc2)cc1F] | ESIMS m/z 373 ([M + H]$^+$) | 140-143 | white solid | (DMSO-d$_6$) 8.71 (s, 1H), 8.45 (d, J = 1.7 Hz, 1H), 7.52 (d, J = 1.2 Hz, 4H), 5.23 (s, 2H), 3.24 (s, 3H), 3.13 (s, 3H) |
| 32 | 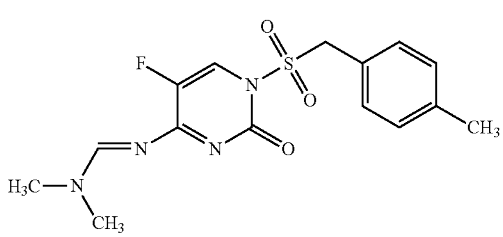 | ESIMS m/z 353 ([M + H]$^+$) | 150-152 | white solid | (DMSO-d$_6$) 8.71 (s, 1H), 8.44 (d, J = 1.9 Hz, 1H), 7.37 (d, J = 7.8 Hz, 2H), 7.22 (d, J = 7.9 Hz, 2H), 5.14 (s, 2H), 3.24 (s, 3H), 3.13 (s, 3H), 2.31 (s, 3H) |
| 34 | 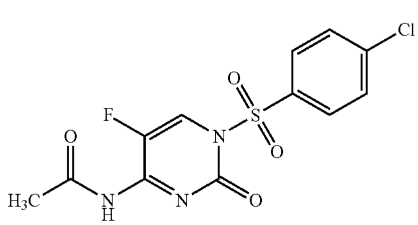 [SMILES: CC(=O)Nc1nc(=O)n(S(=O)(=O)c2ccc(Cl)cc2)cc1F] | ESIMS m/z 346 ([M + H]$^+$), 344 ([M − H]$^-$) | 159-162 | tan solid | 8.27 (d, J = 5.5 Hz, 1H), 8.07 (d, J = 8.7 Hz, 2H), 7.80 (s, 1H), 7.57 (d, J = 8.7 Hz, 2H), 2.62 (s, 3H) |

TABLE I-continued

Compounds and Related Characterization Data

| Cmpd | Structure | MS | mp (° C.) | Appearance | ¹H NMR* (δ, CDCl₃) |
|---|---|---|---|---|---|
| 35 | 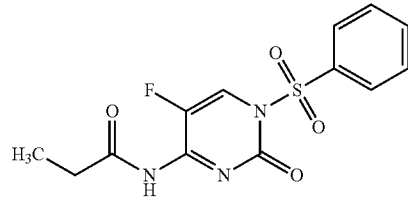 | ESIMS m/z 360 ([M + H]⁺), 358 ([M − H]⁻) | 148-154 dec | yellow solid | (DMSO-d₆) 10.83 (s, 1H), 8.61 (d, J = 6.0 Hz, 1H), 8.10 (d, J = 8.6 Hz, 2H), 7.79 (d, J = 8.6 Hz, 2H), 2.63 (q, J = 7.3 Hz, 2H), 1.01 (t, J = 7.3 Hz, 3H) |
| 36 | 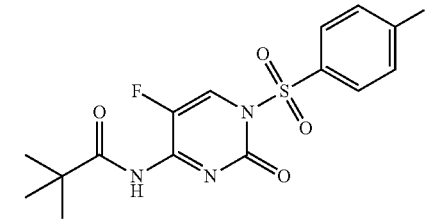 | ESIMS m/z 388 ([M + H]⁺), 386 ([M − H]⁻) | 129-132 | light yellow solid | 8.16 (d, J = 5.5 Hz, 1H), 8.04 (d, J = 8.8 Hz, 2H), 7.56 (d, J = 8.9 Hz, 2H), 1.24 (s, 9H) |
| 37 | 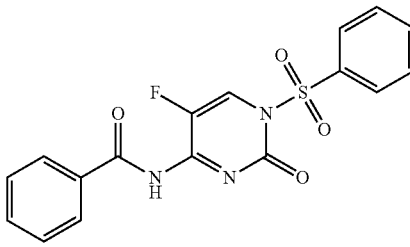 | ESIMS m/z 408 ([M + H]⁺), 406 ([M − H]⁻) | 156-159 | white solid | 12.64 (s, 1H), 8.25 (d, J = 7.6 Hz, 2H), 8.18 (d, J = 5.5 Hz, 1H), 8.05 (m, 2H), 7.58 (m, 3H), 7.46 (t, J = 7.6 Hz, 2H) |
| 39 | 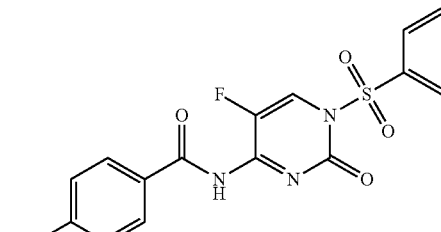 | ESIMS m/z 422 ([M + H]⁺), 420 ([M − H]⁻) | 156-158 | tan solid | 12.50 (s, 1H), 8.15 (m, 3H), 8.05 (d, J = 8.7 Hz, 2H), 7.59 (d, J = 8.7 Hz, 2H), 7.25 (d, J = 6.9 Hz, 2H), 2.42 (s, 3H) |
| 41 | 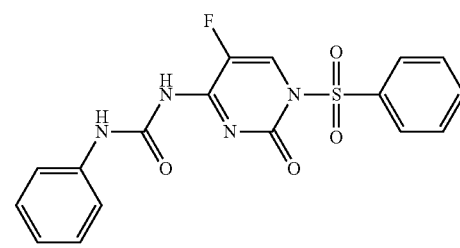 | ESIMS m/z 423 ([M + H]⁺) | 211-214 | pale yellow solid | (DMSO-d₆) 11.26 (s, 1H), 10.90 (s, 1H), 8.64 (d, J = 5.6 Hz, 1H), 8.11 (d, J = 8.6 Hz, 2H), 7.81 (d, J = 8.7 Hz, 2H), 7.45 (d, J = 7.6 Hz, 2H), 7.35 (t, J = 7.3 Hz, 2H), 7.11 (s, 1H) |
| 42 | 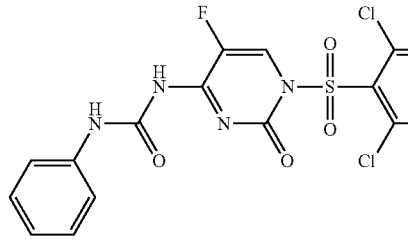 | ESIMS m/z 457 ([M + H]⁺) | 205-210 | white solid | (DMSO-d₆) 11.19 (s, 1H), 11.02 (s, 1H), 8.72 (s, 1H), 7.76 (m, 3H), 7.47 (d, J = 8.4 Hz, 2H), 7.34 (t, J = 7.5 Hz, 2H), 7.10 (m, 1H) |

TABLE I-continued

Compounds and Related Characterization Data

| Cmpd | Structure | MS | mp (° C.) | Appearance | $^1$H NMR* (δ, CDCl$_3$) |
|---|---|---|---|---|---|
| 43 | 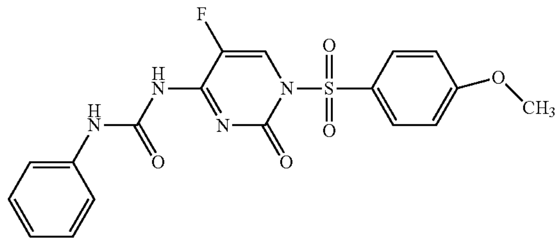 [SMILES: COc1ccc(S(=O)(=O)n2cc(F)c(NC(=O)Nc3ccccc3)nc2=O)cc1] | ESIMS m/z 419 ([M + H]$^+$) | 185-191 | white solid | |
| 45 | 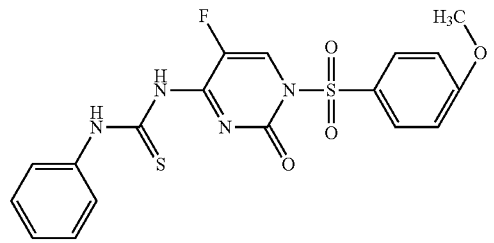 [SMILES: COc1ccc(S(=O)(=O)n2cc(F)c(NC(=S)Nc3ccccc3)nc2=O)cc1] | ESIMS m/z 435 ([M + H]$^+$) | 190-195 | light brown solid | (DMSO-d$_6$) 11.31 (s, 1H), 10.84 (s, 1H), 8.62 (s, 1H), 8.03 (d, J = 8.8 Hz, 2H), 7.44 (s, 2H), 7.35 (s, 2H), 7.21 (d, J = 8.7 Hz, 2H), 7.10 (s, 1H), 3.89 (s, 3H) |
| 46 | 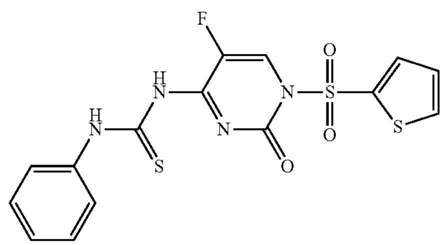 [SMILES: O=c1nc(NC(=S)Nc2ccccc2)c(F)cn1S(=O)(=O)c1cccs1] | ESIMS m/z 411 ([M + H]$^+$) | 182-185 | pale yellow solid | (DMSO-d$_6$) 11.28 (s, 1H), 10.87 (s, 1H), 8.61 (s, 1H), 8.29 (dd, J = 5.0. 1.4 Hz, 1H), 8.08 (d, J = 2.7 Hz, 1H), 7.46 (m, 2H), 7.34 (m, 4H) |
| 48 | 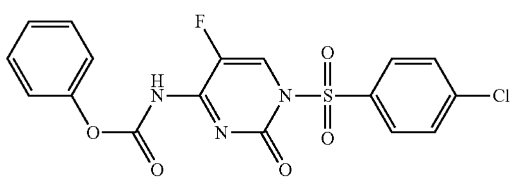 [SMILES: O=C(Nc1nc(=O)n(S(=O)(=O)c2ccc(Cl)cc2)cc1F)Oc1ccccc1] | ESIMS m/z 424 ([M + H]$^+$) | 192-195 | pale yellow solid | (DMSO-d$_6$) 7.97 (m, 2H), 7.85 (m, 1H), 7.69 (m, 2H), 7.34 (dd, J = 10.9, 5.0 Hz, 2H), 7.15 (t, J = 7.3 Hz, 1H), 7.06 (m, 2H) |
| 49 | 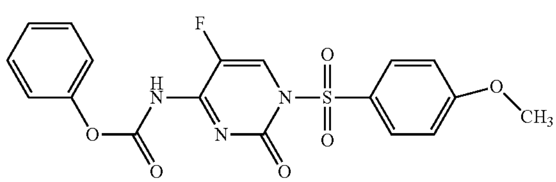 [SMILES: COc1ccc(S(=O)(=O)n2cc(F)c(NC(=O)Oc3ccccc3)nc2=O)cc1] | ESIMS m/z 420 ([M + H]$^+$), 418 ([M − H]$^−$) | 138-142 | pale yellow solid | (DMSO-d$_6$) δ 7.89 (m, 2H), 7.84 (d, J = 7.1 Hz, 1H), 7.33 (t, J = 7.9 Hz, 2H), 7.13 (m, 3H), 7.06 (dd, J = 7.6, 0.9 Hz, 2H), 3.85 (s, 3H) |
| 50 | 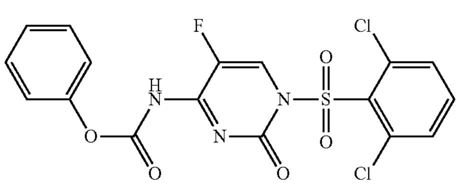 [SMILES: O=C(Nc1nc(=O)n(S(=O)(=O)c2c(Cl)cccc2Cl)cc1F)Oc1ccccc1] | ESIMS m/z 458 ([M + H]$^+$) | 199-203 | pale yellow solid | (DMSO-d$_6$) 8.10 (m, 1H), 7.89 (m, 1H), 7.80 (d, J = 7.0 Hz, 1H), 7.35 (t, J = 7.9 Hz, 3H), 7.21 (dd, J = 4.9, 3.9 Hz, 1H), 7.15 (dd, J = 11.5, 4.2 Hz, 1H), 7.07 (m, 2H) |

*All $^1$H NMR spectra were recorded in CDCl$_3$ at 300 or 400 MHz unless otherwise stated.

Example 11

Evaluation of Fungicidal Activity: Leaf Blotch of Wheat (*Mycosphaerella graminicola*; Anamorph: *Septoria tritici*; Bayer Code SEPTTR)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber) to permit spores to germinate and infect the leaf. The plants were then transferred to a greenhouse for disease to develop.

The following table presents the activity of typical compounds of the present disclosure when evaluated in these experiments. The effectiveness of the test compounds in controlling disease was determined by assessing the severity of disease on treated plants, then converting the severity to percent control based on the level of disease on untreated, inoculated plants.

In each case of Table II the rating scale is as follows:

| % Disease Control | Rating |
|---|---|
| 76-100 | A |
| 51-75 | B |
| 26-50 | C |
| 0-25 | D |
| Not Tested | E |

TABLE II

One-Day Protectant (1DP) and Three-Day Curative (3DC) Activity of Compounds on SEPTTR at 100 ppm

| Cmpd | SEPTTR 100 PPM 1DP | SEPTTR 100 PPM 3DC |
|---|---|---|
| 1 | A | A |
| 2 | A | A |
| 3 | A | A |
| 4 | A | A |
| 5 | A | A |
| 6 | A | A |
| 7 | A | A |
| 8 | A | A |
| 9 | A | A |
| 10 | A | A |
| 11 | C | C |
| 12 | A | A |
| 13 | A | A |
| 14 | A | A |
| 15 | B | A |
| 16 | B | A |
| 17 | A | A |
| 18 | A | A |
| 19 | A | A |
| 20 | E | E |
| 21 | E | E |
| 22 | A | A |
| 23 | A | A |
| 24 | A | A |
| 25 | A | A |
| 26 | A | A |
| 27 | A | A |
| 28 | C | B |
| 29 | A | A |
| 30 | E | E |
| 31 | E | E |
| 32 | E | E |
| 33 | A | C |
| 34 | A | A |
| 35 | A | A |
| 36 | A | A |
| 37 | A | C |
| 38 | A | D |
| 39 | D | A |
| 40 | D | C |
| 41 | E | E |
| 42 | D | C |
| 43 | D | C |
| 44 | D | C |
| 45 | C | B |
| 46 | D | C |
| 47 | B | A |
| 48 | E | E |

TABLE II-continued

One-Day Protectant (1DP) and Three-Day Curative (3DC) Activity of Compounds on SEPTTR at 100 ppm

| Cmpd | SEPTTR 100 PPM 1DP | SEPTTR 100 PPM 3DC |
|---|---|---|
| 49 | D | A |
| 50 | A | A |

What is claimed is:
1. A compound of Formula I:

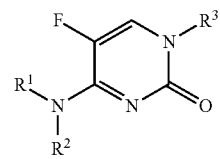

Formula I or a salt thereof, wherein $R^1$ is:
H;
$C_1$-$C_6$ alkyl optionally substituted with 1-3 $R^4$;
$C_2$-$C_6$ alkenyl optionally substituted with 1-3 $R^4$;
$C_3$-$C_6$ alkynyl optionally substituted with 1-3 $R^4$;
phenyl or benzyl wherein each of the phenyl or the benzyl is optionally substituted with 1-3 $R^5$, or with a 5- or 6-membered saturated or unsaturated ring system, or with a 5-6 fused ring system, or with a 6-6 fused ring system each containing 1-3 heteroatoms wherein each ring is optionally substituted with 1-3 $R^5$, biphenyl or naphthyl optionally substituted with 1-3 $R^5$;
—(CHR$^6$)$_m$OR$^7$;
—C(=O)R$^8$;
—C(=S)R$^8$;
—C(=S)OR$^8$;
—S(O)2R$^8$;
—(CHR6)$_m$N(R$^9$)R$^{10}$;
—C(=O)N(R$^9$)R$^{10}$; or
—C(=S)N(R$^9$)R$^{10}$;
wherein m is an integer 1-3;
$R^2$ is H or $C_1$-$C_6$ alkyl optionally substituted with $R^4$;
alternatively R1 and R2 are taken together to form =CR$^{11}$N(R$^{12}$)R$^{13}$;
$R^3$ is —S(O)$_2$R$^{14}$;
$R^4$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, haloalkylthio, amino, halothio, $C_1$-$C_3$ alkylamino, $C_2$-$C_6$ alkoxycarbonyl, $C_2$-$C_6$ alkylcarbonyl, $C_2$-$C_6$ alkylaminocarbonyl, hydroxyl, or $C_3$-$C_6$ trialkylsilyl;
$R^5$ is independently halogen, $C_1$-$C_5$ alkyl, $C_1$-$C_6$ haloalkyl, $C_1$-$C_5$ alkoxy, $C_1$-$C_6$ haloalkoxy, $C_1$-$C_6$ alkylthio, $C_1$-$C_6$ haloalkylthio, halothio, amino, $C_1$-$C_6$ alkylamino, $C_2$-$C_6$ dialkylamino, $C_2$-$C_6$ alkoxycarbonyl, $C_1$-$C_6$ alkylsulfonyl or $C_2$-$C_6$ alkylcarbonyl, nitro, hydroxyl, or cyano;
$R^6$ is H, $C_1$-$C_6$ alkyl, $C_1$-$C_6$ alkoxy, phenyl or benzyl wherein each of the benzyl or the phenyl is optionally substituted with 1-3 $R^5$;
$R^7$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, $C_2$-$C_6$ alkylcarbonyl, phenyl or benzyl wherein each of the phenyl or the benzyl is optionally substituted with 1-3 $R^5$, or with a 5- or 6-membered saturated or unsaturated ring system, or with 5-6 fused ring system, or with a 6-6 fused ring system each containing 1-3 heteroatoms wherein each ring is optionally substituted with 1-3 $R^5$, biphenyl or naphthyl optionally substituted with 1-3 $R^5$;

$R^8$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, phenyl or benzyl wherein each of the phenyl or the benzyl is optionally substituted with 1-3 R5, or with a 5- or 6-membered saturated or unsaturated ring system, or with a 5-6 fused ring system, or 6-6 fused ring system each containing 1-3 heteroatoms wherein each ring is optionally substituted with 1-3 $R^5$, biphenyl or naphthyl optionally substituted with 1-3 R5;

$R^9$ is H, $C_1$-$C_6$, alkyl, $C_1$-$C_6$ haloalkyl, $C_1$-$C_6$ alkoxyalkyl, $C_2$-$C_6$ alkylcarbonyl, phenyl or benzyl wherein each of the phenyl or the benzyl is optionally substituted with 1-3 $R^5$, or with a 5- or 6-membered saturated or unsaturated ring system, or with a 5-6 fused ring system, or with a 6-6 fused ring system each containing 1-3 heteroatoms wherein each ring is optionally substituted with 1-3 $R^5$, biphenyl or naphthyl optionally substituted with 1-3 $R^5$;

$R^{10}$ is H, $C_1$-$C_6$ alkyl, $C_1$-$C_6$ haloalkyl, $C_1$-$C_6$ alkoxyalkyl, $C_2$-$C_6$ alkylcarbonyl, or benzyl, wherein the benzyl is optionally substituted with 1-3 $R^5$;

alternatively $R^9$ and $R^{10}$ are taken together to form a 5- or 6-membered saturated or unsaturated ring containing 1-3 heteroatoms wherein each ring is optionally substituted with 1-3 $R^5$;

$R^{11}$ is H or $C_1$-$C_4$ alkyl;

$R^{12}$ is H, cyano, hydroxyl, $C_1$-$C_4$ alkyl, $C_1$-$C_6$ alkoxy, $C_2$-$C_6$ alkylcarbonyl, phenyl or benzyl wherein each of the phenyl or the benzyl is optionally substituted with 1-3 $R^5$;

alternatively $R^{11}$ and $R^{12}$ are taken together to form a 5- or 6-membered saturated or unsaturated ring containing 1-3 heteroatoms wherein each ring is optionally substituted with 1-3 $R^5$;

$R^{13}$ is H, $C_1$-$C_4$ alkyl, $C_1$-$C_6$ alkoxy, $C_2$-$C_6$ alkylcarbonyl, phenyl or benzyl wherein each of the phenyl or the benzyl is optionally substituted with 1-3 $R^5$;

alternatively $R^{12}$ and $R^{13}$ are taken together to form a 5- or 6-membered saturated or unsaturated ring containing 1-3 heteroatoms wherein each ring is optionally substituted with 1-3 $R^5$; and $R^{14}$ is $C_1$-$C_6$ alkyl, $C_1$-$C_6$ haloalkyl, amino, $C_1$-$C_6$ alkylamino, $C_2$-$C_6$ dialkylamino, a phenyl or benzyl wherein each of the phenyl or the benzyl is optionally substituted with 1-3 $R^5$, 4-(3-chloro-5-(trifluoromethyl)pyridin-2-yloxy)-3-methylphenyl, 4-(3-chloro-5-(trifluoromethyl)pyridin-2-yloxy)-2-methylphenyl, or a 5- or 6-membered saturated or unsaturated ring containing 1-3 heteroatoms wherein each ring is optionally substituted with 1-3 $R^5$.

2. A composition for the control of a fungal pathogen comprising the compound of claim 1 and a phytologically acceptable carrier material.

3. The composition of claim 2 wherein the fungal pathogen is Apple Scab (*Venturia inaequalis*), Leaf Blotch of Wheat (*Septoria tritici*), Leaf Spot of Sugarbeets (*Cercospora beticola*), Leaf Spots of Peanut (*Cercospora arachidicola* and *Cercosporidium personatum*), and Black Sigatoka of Banana (*Mycosphaerellafijiensis*).

4. A method for the control and prevention of fungal attack on a plant, the method including the steps of:
applying a fungicidally effective amount of at least one of the compounds of claim 1 to at least one of the group consisting of: the plant, an area adjacent to the plant, a soil adapted to support growth of the plant, a root of the plant, a foliage of the plant, and a seed adapted to produce the plant.

5. The compound of claim 1, wherein $R^1$ is selected from the group consisting of:
H;
$C_1$-$C_6$ alkyl optionally substituted with 1-3 $R^4$;
$C_2$-$C_6$ alkenyl optionally substituted with 1-3 $R^4$;
$C_3$-$C_6$ alkynyl optionally substituted with 1-3 $R^4$; and
phenyl or benzyl wherein each of the phenyl or the benzyl is optionally substituted with 1-3 $R^5$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^5$, biphenyl or naphthyl optionally substituted with 1-3 $R^5$.

6. The compound of claim 1, wherein $R^2$ is $C_1$-$C_6$ alkyl optionally substituted with $R^4$.

7. The compound of claim 1 in the form of a salt.

8. The compound of claim 1, wherein $R^1$ and $R^2$ are taken together to form =$CR^{11}N(R^{12})R^{13}$ and $R^3$ is —$S(O)_2R^{14}$.

9. The compound of claim 1, wherein $R^1$ is H, $R^2$ is H, and $R^3$ is —$S(O)_2R^{14}$.

10. The compound of claim 1, wherein $R^1$ is —C(=O)$R^8$, $R^2$ is H, and $R^3$ is —$S(O)_2R^{14}$.

11. The compound of claim 1, wherein $R^1$ is —C(=O)N($R^9$)$R^{10}$, $R^2$ is H, and $R^3$ is —$S(O)_2R^{14}$.

12. The compound of claim 1, wherein $R^1$ is —C(=S)N($R^9$)$R^{10}$, $R^2$ is H, and $R^3$ is —$S(O)_2R^{14}$.

13. The compound of claim 1, wherein $R^1$ is —C(=O)O$R^8$, $R^2$ is H, and $R^3$ is —$S(O)_2R^{14}$.

* * * * *

UNITED STATES PATENT AND TRADEMARK OFFICE
CERTIFICATE OF CORRECTION

PATENT NO. : 9,862,686 B2
APPLICATION NO. : 14/661274
DATED : January 9, 2018
INVENTOR(S) : Timothy Boebel et al.

Page 1 of 1

It is certified that error appears in the above-identified patent and that said Letters Patent is hereby corrected as shown below:

On the Title Page

Item (71) Applicant's address should be revised to read:
P.O. Box 60, Beer Sheva, Israel, 84100.

Signed and Sealed this
Eleventh Day of June, 2019

Andrei Iancu
*Director of the United States Patent and Trademark Office*